US012731661B2

(12) United States Patent
Kappel

(10) Patent No.: US 12,731,661 B2
(45) Date of Patent: Sep. 8, 2026

(54) SYSTEM AND METHOD FOR TRAINING MACHINE-LEARNING ALGORITHMS FOR PROCESSING BIOLOGY-RELATED DATA, A MICROSCOPE AND A TRAINED MACHINE LEARNING ALGORITHM

(71) Applicant: Leica Microsystems CMS GmbH, Wetzlar (DE)

(72) Inventor: Constantin Kappel, Schriesheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 1283 days.

(21) Appl. No.: 17/596,290

(22) PCT Filed: Jun. 7, 2019

(86) PCT No.: PCT/EP2019/064960
§ 371 (c)(1),
(2) Date: Dec. 7, 2021

(87) PCT Pub. No.: WO2020/244774
PCT Pub. Date: Dec. 10, 2020

(65) Prior Publication Data
US 2022/0246244 A1 Aug. 4, 2022

(51) Int. Cl.
*G16B 40/20* (2019.01)
*G06F 18/22* (2023.01)
(Continued)

(52) U.S. Cl.
CPC ............. *G16B 40/20* (2019.02); *G06F 18/22* (2023.01); *G06N 3/044* (2023.01); *G06N 3/045* (2023.01);
(Continued)

(58) Field of Classification Search
CPC ........ G16B 40/20; G16B 30/20; G16B 40/30; G06F 18/22; G06N 3/044; G06N 3/045;
(Continued)

(56) References Cited

U.S. PATENT DOCUMENTS 10,127,475 B1 * 11/2018 Corrado ................ G06F 18/214
10,134,131 B1 11/2018 Ando et al.
(Continued)

FOREIGN PATENT DOCUMENTS

WO 2018091486 A1 5/2018

OTHER PUBLICATIONS

Wang, Jiabao, Learning deep discriminative features based on cosine loss function, Jul. 6, 2017, Electronics Letters, vol. 53, No. 14, p. 918-920 (Year: 2017).*
(Continued)

*Primary Examiner* — Ryan J. Walters
(74) *Attorney, Agent, or Firm* — 2SPL Patent Attorneys PartG mbB; Kieran O'Leary

(57) ABSTRACT

A system (100) comprises one or more processors (110) and one or more storage devices (120), wherein the system (100) is configured to generate a first high-dimensional representation of the biology-related language-based input training data (102) by a language recognition machine-learning algorithm executed by the one or more processors (110). Further, the system (100) is configured to generate biology-related language-based output training data based on the first high-dimensional representation by the language recognition machine-learning algorithm and adjust the language recognition machine-learning algorithm based on a comparison of the biology-related language-based input training data (102) and the biolo-gy-related language-based output training data. Additionally, the system (100) is configured to generate a second high-dimensional representation of the
(Continued)

biology-related image-based input training data (104) by a visual recognition machine-learning algorithm executed by the one or more processors (110) and adjust the visual recognition machine-learning algorithm based on a comparison of the first high-dimensional representation and the second high-dimensional representation.

29 Claims, 10 Drawing Sheets

(51) Int. Cl.

| | |
|---|---|
| ***G06N 3/044*** | (2023.01) |
| ***G06N 3/045*** | (2023.01) |
| ***G06N 3/048*** | (2023.01) |
| ***G06N 3/063*** | (2023.01) |
| ***G06N 3/08*** | (2023.01) |
| ***G16B 30/20*** | (2019.01) |
| ***G16B 40/30*** | (2019.01) |
| *G06N 5/01* | (2023.01) |
| *G06N 20/10* | (2019.01) |
| *G06N 20/20* | (2019.01) |

(52) U.S. Cl.

CPC ............ *G06N 3/048* (2023.01); *G06N 3/063* (2013.01); *G06N 3/08* (2013.01); *G16B 30/20* (2019.02); *G16B 40/30* (2019.02); *G06N 5/01* (2023.01); *G06N 20/10* (2019.01); *G06N 20/20* (2019.01)

(58) Field of Classification Search

CPC .......... G06N 3/048; G06N 3/063; G06N 3/08; G06N 5/01; G06N 20/10; G06N 20/20

See application file for complete search history.

(56) References Cited

U.S. PATENT DOCUMENTS

| | | | | |
|---|---|---|---|---|
| 11,960,518 | B2 * | 4/2024 | Kappel | G16H 30/20 |
| 12,026,191 | B2 * | 7/2024 | Kappel | G16H 30/20 |
| 12,272,161 | B2 * | 4/2025 | Kappel | G06V 10/82 |
| 2017/0249548 | A1 | 8/2017 | Nelson | |
| 2024/0331417 | A1 * | 10/2024 | Kappel | G16B 40/30 |

OTHER PUBLICATIONS

Mendieta et al., A cross-modal transfer approach . . . , 2017.
Socher et al., Zero-Shot Learning Through Cross-Modal Transfer, Mar. 20, 2013.
Frome et al.: "DeViSE: a Deep Visual-Semantic Embedding Model".
Socher et al.: "Zero-Shot Learning Through Cross-Modal Transfer".
Milton et al.: "A cross-modal transfer approach for histological images . . . ".
Yongqin et al.: "Latent Embeddings for Zero-Shot Classification".
Danny et al.: "Embedding Images and Sentences in a Common Space with a Recurrent Capsule Network".
Dai et al.: "Transformer-XL: Attentive Language Models Beyond a Fixed-Length Context".

* cited by examiner

FIG. 1

210
GATTACA

Figure 4:
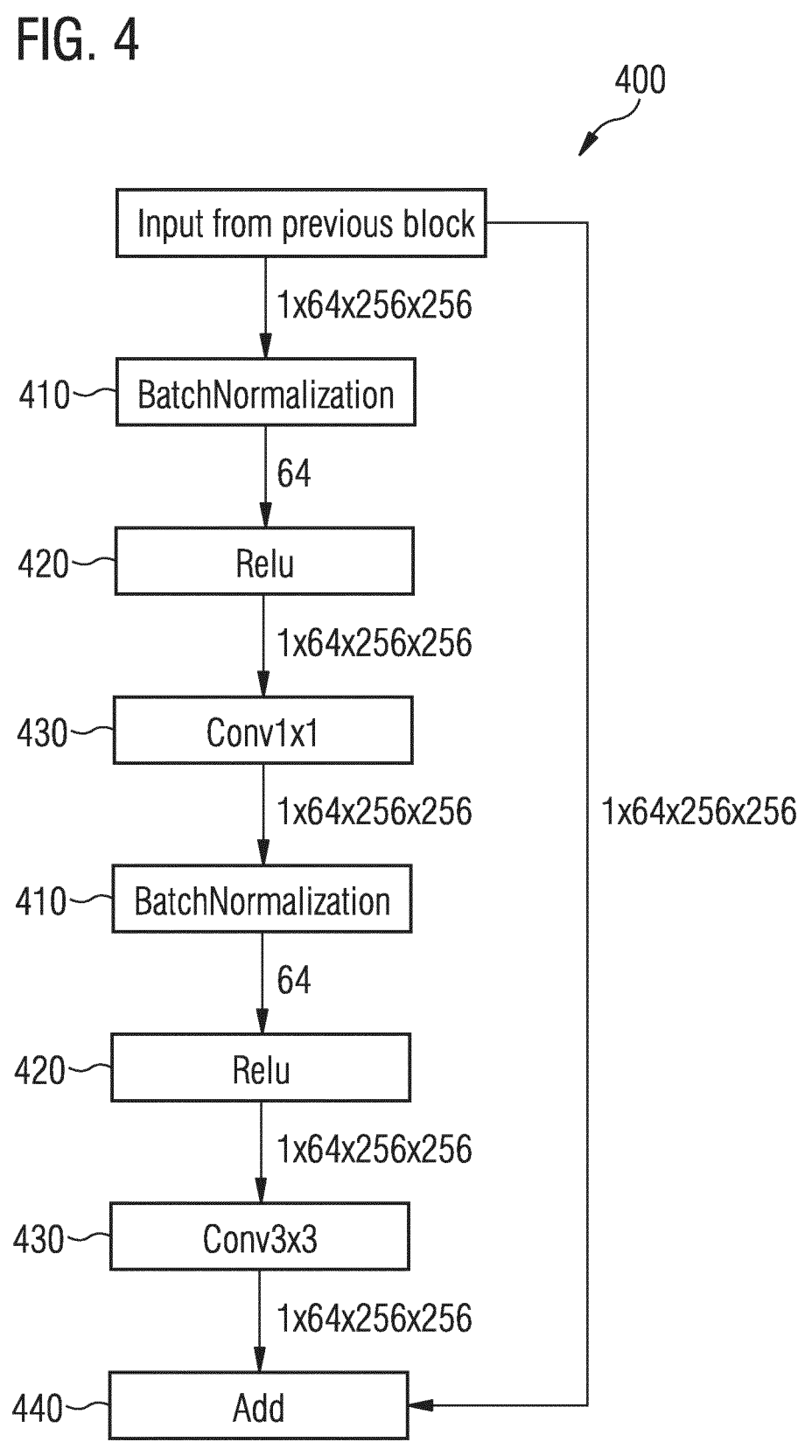

Input from previous block

1x64x256x256

410 BatchNormalization

64

420 Relu

1x64x256x256

430 Conv1x1

1x64x256x256

1x64x256x256

410 BatchNormalization

64

420 Relu

1x64x256x256

430 Conv3x3

1x64x256x256

440 Add

Figure 6:
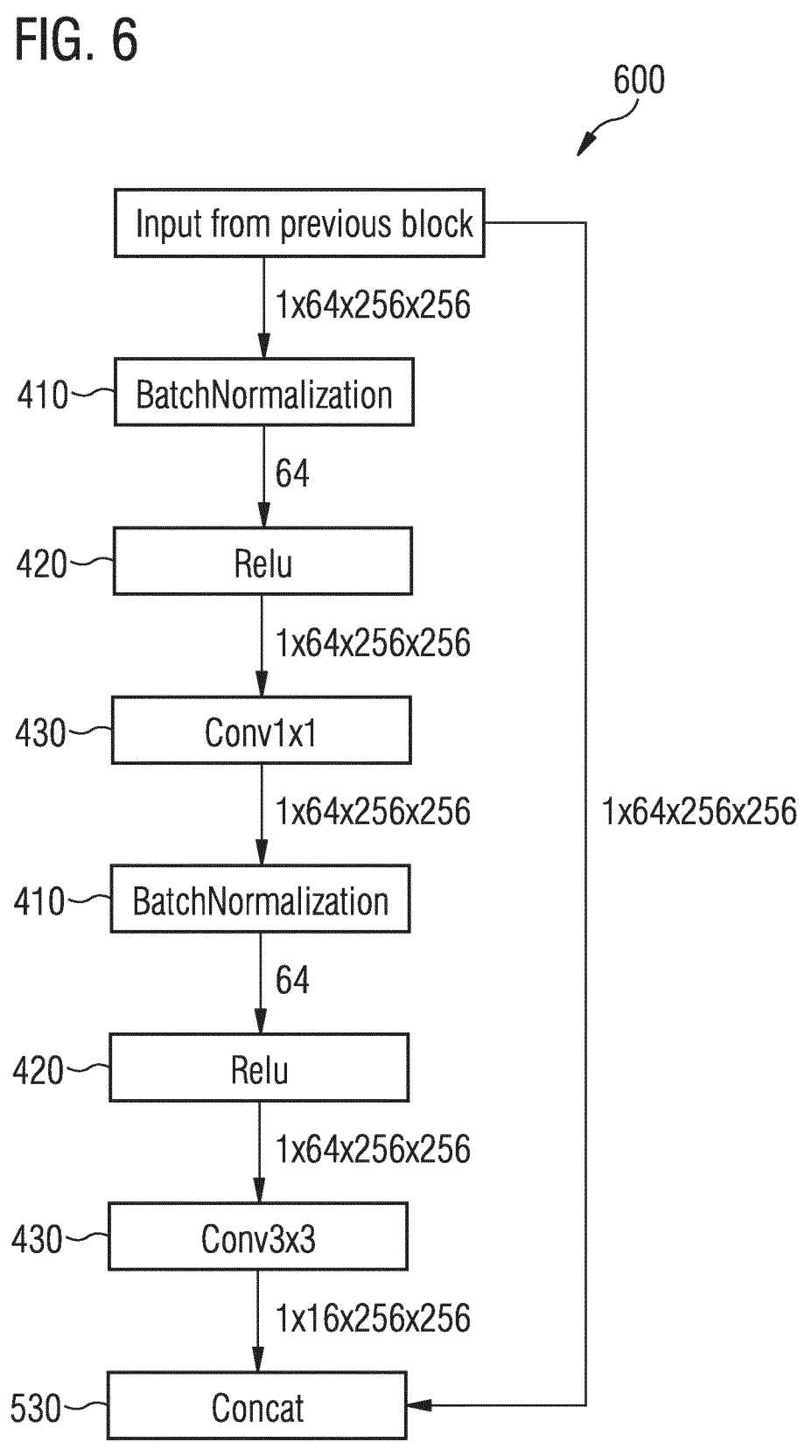

Input from previous block

1x64x256x256

410 BatchNormalization

64

420 Relu

1x64x256x256

430 Conv1x1

1x64x256x256

1x64x256x256

410 BatchNormalization

64

420 Relu

1x64x256x256

430 Conv3x3

1x16x256x256

530 Concat

700
Input from previous block
1x64x256x256
410
BatchNormalization
64
420
Relu
1x64x256x256
430
Conv1x1
1x64x256x256
410
BatchNormalization
64
420
Relu
1x16x256x256
430
1x16x256x256
Conv3x3
1x64x256x256
510
GlobalAveragePool
520
GlobalMaxPool
1x16x1x1
1x16x1x1
530
Concat
1x32x1x1
430
Conv1x1
1x32x1x1
420
Relu
1x32x1x1
1x16x
256x256
1x64x
256x256

430
Conv1x1
1x16x1x1
540
Sigmoid
1x16x1x1
550
Mul
1x16x256x256
410
16
BatchNormalization
560
Mean
570
16
Max
1x1x256x256
530
1x1x256x256
Concat
16
1x2x256x256
430
Conv7x7
1x16x256x256
540
Sigmoid
1x16x256x256
550
Mul
1x16x256x256
530
Concat

900

910

920

930

940

950

960

970

SYSTEM AND METHOD FOR TRAINING MACHINE-LEARNING ALGORITHMS FOR PROCESSING BIOLOGY-RELATED DATA, A MICROSCOPE AND A TRAINED MACHINE LEARNING ALGORITHM

TECHNICAL FIELD

Examples relate to the processing of biology-related data.

BACKGROUND

In many biological applications, a vast amount of data is generated. For example, images are taken from a huge amount of biological structures and stored in databases. It is very time-consuming and expensive to analyse the biological data manually.

SUMMARY

Hence, there is a need for an improved concept for processing biology-related data.

This need may be satisfied by the subject matter of the claims.

Some embodiments relate to a system comprising one or more processors and one or more storage devices. The system is configured to receive biology-related language-based input training data and generate a first high-dimensional representation of the biology-related language-based input training data by a language recognition machine-learning algorithm executed by the one or more processors. The first high-dimensional representation comprises at least three entries each having a different value. Further, the system is configured to generate biology-related language-based output training data based on the first high-dimensional representation by the language recognition machine-learning algorithm executed by the one or more processors and to adjust the language recognition machine-learning algorithm based on a comparison of the biology-related language-based input training data and the biology-related language-based output training data. Additionally, the system is configured to receive biology-related image-based input training data associated with the biology-related language-based input training data and to generate a second high-dimensional representation of the biology-related image-based input training data by a visual recognition machine-learning algorithm executed by the one or more processors. The second high-dimensional representation comprises at least three entries each having a different value. Further, the system is configured to adjust the visual recognition machine-learning algorithm based on a comparison of the first high-dimensional representation and the second high-dimensional representation.

By using a language recognition machine-learning algorithm textual biological input can be mapped to a high-dimensional representation. By allowing the high-dimensional representation to have entries with various different values (in contrast to one hot encoded representations), semantically similar biological inputs can be mapped to similar high-dimensional representations. By training a visual recognition machine-learning algorithm to map images to the high-dimensional representations trained by the language recognition machine-learning algorithm, images with similar biological content can be mapped to similar high-dimensional representations as well. Consequently, the likelihood of a semantically correct or at least semantically close classification of images by a correspondingly trained visual recognition machine-learning algorithm may be significantly improved. Further, it may be possible for the correspondingly trained visual recognition machine-learning algorithm to map untrained images more accurately to a high-dimensional representation close to high-dimensional representation of similar meaning or to a semantically matching high-dimensional representation. A trained language recognition machine-learning algorithm and/or a trained visual recognition machine-learning algorithm may be obtained by the proposed concept, which may be able to provide a semantically correct or very accurate classification of biology-related language-based and/or image-based input data. The trained language recognition machine-learning algorithm and/or the trained visual recognition machine-learning algorithm may enable a search of biology-related images among a plurality of biological images based on a language-based search input or an image-based search input, tagging of biology-related images, finding or generating typical images and/or similar applications.

SHORT DESCRIPTION OF THE FIGURES

Some examples of apparatuses and/or methods will be described in the following by way of example only, and with reference to the accompanying figures, in which FIG. 1 is a schematic illustration of a system for training machine-learning algorithms for processing biology-related data;

FIG. 4 is a computational graph of a part of a visual recognition neural network based on a ResNet architecture;

FIG. 6 is a computational graph of a part of a visual recognition neural network based on a DenseNet architecture;

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figures 1, 5:
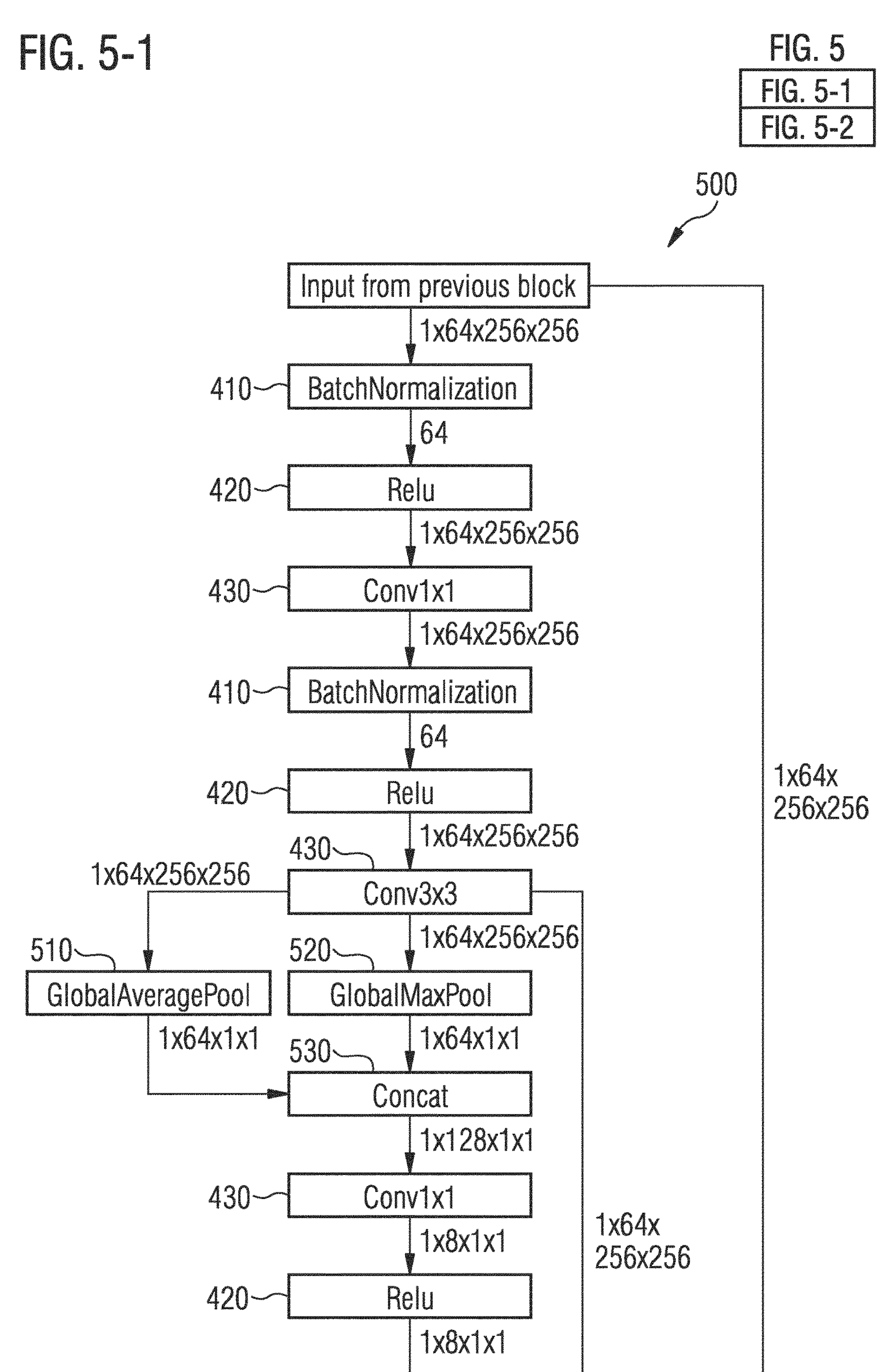
FIG. 5 is a computational graph of a part of a visual recognition neural network based on a ResNet architecture with modified CBAM block.
Figures 2, 5:
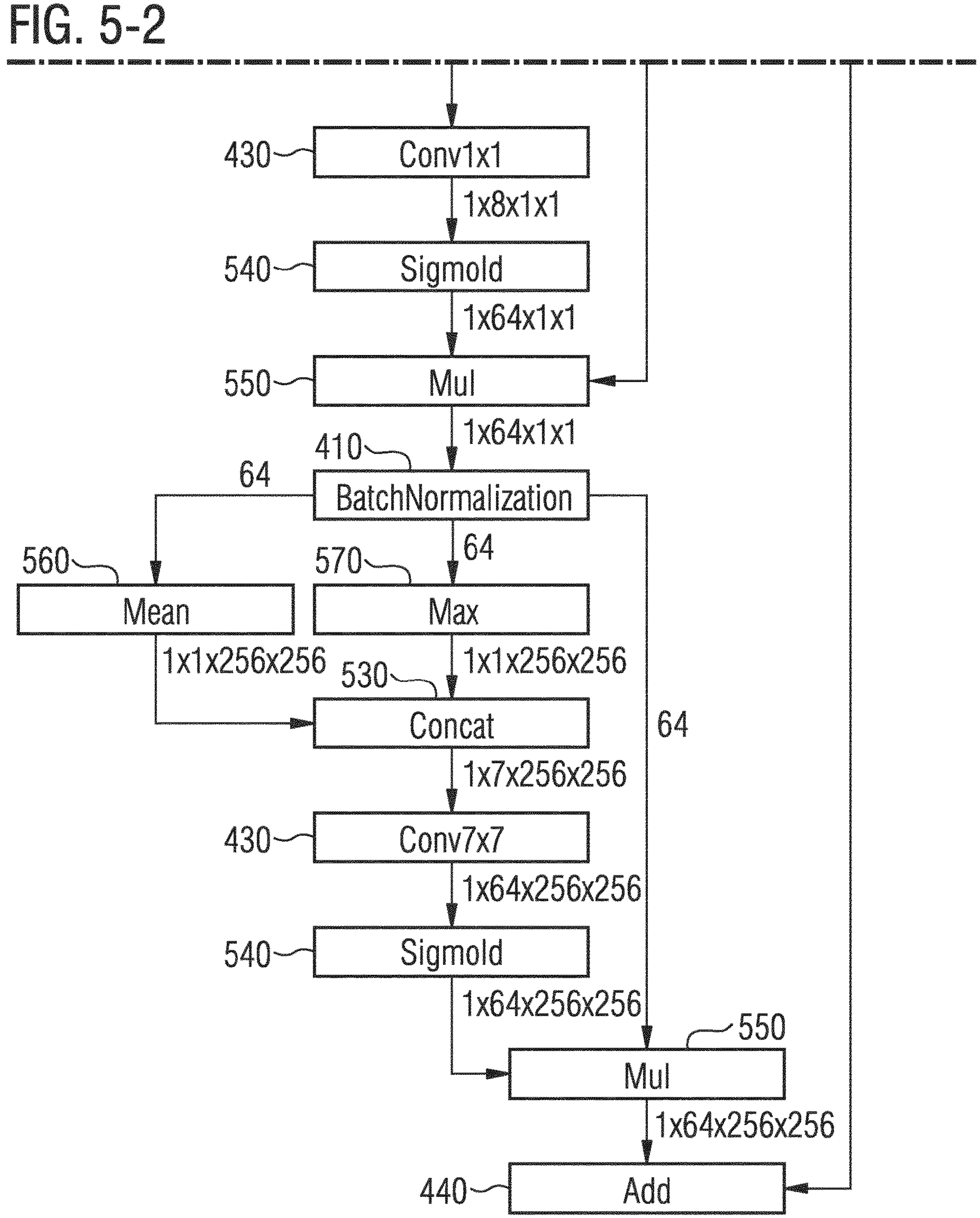

FIG. 1 shows a schematic illustration of a system 100 for training machine-learning algorithms for processing biology-related data according to an embodiment. The system 100 comprises one or more processors 110 and one or more storage devices 120. The system 100 is configured to receive biology-related language-based input training data 102. Additionally, the system 100 is configured to generate a first high-dimensional representation of the biology-related language-based input training data 102 by a language recognition machine-learning algorithm executed by the one or more processors 110. The first high-dimensional representation comprises at least three entries each having a different value (or at least 20 entries, at least 50 entries or at least 100 entries having values different from each other). Further, the system 100 is configured to generate biology-related language-based output training data based on the first high-dimensional representation by the language recognition machine-learning algorithm executed by the one or more processors 110. In addition, the system 100 is configured to adjust the language recognition machine-learning algorithm based on a comparison of the biology-related language-based input training data 102 and the biology-related language-based output training data. Additionally, the system 100 is configured to receive biology-related image-based input training data 104 associated with the biology-related language-based input training data 102. Further, the system 100 is configured to generate a second high-dimensional representation of the biology-related image-based input training data 104 by a visual recognition machine-learning algorithm executed by the one or more processors 110. The second high-dimensional representation comprises at least three entries each having a different value (or at least 20 entries, at least 50 entries or at least 100 entries having values different from each other). Further, the system 100 is configured to adjust the visual recognition machine-learning algorithm based on a comparison of the first high-dimensional representation and the second high-dimensional representation.

The biology-related language-based input training data 102 may be a textual input being related to a biological structure, a biological function, a biological behavior or a biological activity. For example, the biology-related language-based input training data 102 may be a nucleotide sequence, a protein sequence, a description of a biological molecule or biological structure, a description of a behavior of a biological molecule or biological structure, and/or a description of a biological function or a biological activity. The textual input may be natural language, which is descriptive of the biological molecule (e.g. polysaccharide, poly/oligo-nucleotide, protein or lipid) or its behavior in the context of the experiment or data set. It can also be of text as in a nucleotide sequence, a protein sequence or a controlled query language. For example, the biology-related language-based input training data 102 may be a nucleotide sequence or a protein sequence as a huge variety of different sequences is known and available in data bases and/or biological functions and/or activities are known for these sequences. The biology-related language-based input training data 102 may comprise a length of more than 20 characters (or more than 40 characters, more than 60 characters or more than 80 characters). For example, nucleotide sequences (DNA/RNA) are often about three times longer than polypeptide sequences (e.g. peptide, protein), since three base pairs are coded for an amino acid. For example, the biology-related language-based input training data 102 may comprise a length of more than 20 characters, if the biology-related language-based input training data is a protein sequence or an amino acid. The biology-related language-based input training data 102 may comprise a length of more than 60 characters, if the biology-related language-based input training data is a nucleotide sequence or descriptive text in natural language. For example, the biology-related language-based input training data 102 may comprise at least one non-numerical character (e.g. an alphabetical character). The biology-related language-based input training data 102 may also be called token or input token. The biology-related language-based input training data 102 may be received from the one or more storage devices 120, a data base stored by a storage device or may be input by a user. The biology-related language-based input training data may be a first biology-related language-based input training data set (e.g. sequence of input characters, for example, a nucleotide sequence or a protein sequence) of a training group. The training group may comprise a plurality of biology-related language-based input training data sets.

The biology-related language-based output training data may be of the same type as the biology-related language-based input training data 102 including optionally a prediction of a next element. For example, the biology-related language-based input training data 102 may be a biological sequence (e.g. a nucleotide sequence or a protein sequence) and the biology-related language-based output training data may be a biological sequence (e.g. a nucleotide sequence or a protein sequence) as well. The language recognition machine-learning algorithm may be trained so that the biology-related language-based output training data is equal to the biology-related language-based input training data 102 including optionally a prediction of a next element of the biological sequence. In another example, the biology-related language-based input training data 102 may be a biological class of a coarse-grained search term and the biology-related language-based output training data may be a biological class of the coarse-grained search term as well.

Alternatively, the biology-related language-based output training data is of a different type as the biology-related language-based input training data 102. For example, the biology-related language-based input training data 102 is a biological sequence (e.g. a nucleotide sequence or a protein sequence) and the biology-related language-based output training data is a biological class of a coarse-grained search term. In this example, each biological sequence used as input training data 102 may belong to a coarse-grained search term of a group of biological terms and the language recognition machine-learning algorithm may be trained to classify each biological sequence used as input training data to the corresponding coarse-grained search term of the group of biological terms.

A group of biological terms may comprise a plurality of coarse-grained search terms (or alternatively called molecular biological subject heading terms) belonging to the same biological topic. A group of biological terms may be catalytic activity (e.g. as some sort of reaction equation using words for educts and products), pathway (e.g. which pathway is involved, for example, glycolysis), sites and/or regions (e.g. binding site, active site, nucleotide binding site), GO gene ontology (e.g. molecular function, for example, nicotinamide adenine dinucleotide NAD binding, microtubule binding), GO biological function (e.g. apoptosis, gluconeogenesis), enzyme and/or pathway databases (e.g. unique identifiers for sic function, for example, in BRENDA/EC number or UniPathways), subcellular localization (e.g. cytosol, nucleus, cytoskeleton), family and/or domains (e.g. binding sites, motifs, e.g. for posttranslational modification), open-reading frames, single-nucleotide polymorphisms, restriction sites (e.g. oligonucleotides recognized by a restriction enzyme) and/or biosynthesis pathway (e.g. biosynthesis of lipids, polysaccharides, nucleotides or proteins). For example, the group of biological terms may be the group of subcellular localizations and the coarse-grained search terms may be cytosol, nucleus and cytoskeleton.

The biology-related language-based output training data may be generated by a decoder of the language recognition machine-learning algorithm. For example, the biology-related language-based output training data may be generated by applying the language recognition machine-learning algorithm with a current set of parameters (e.g. neural network weights) to generate a first high-dimensional representation. The current set of parameters of the language recognition machine-learning algorithm may be updated during the adjustment of the language recognition machine-learning algorithm.

The biology-related image-based input training data 104 may be image training data (e.g. pixel data of a training image) of an image of a biological structure comprising a nucleotide or a nucleotide sequence, a biological structure comprising a protein or a protein sequence, a biological molecule, a biological tissue, a biological structure with a specific behavior, and/or a biological structure with a specific biological function or a specific biological activity. The biological structure may be a molecule, a viroid or virus, artificial or natural membrane enclosed vesicles, a subcellular structure (like a cell organelle) a cell, a spheroid, an organoid, a three-dimensional cell culture, a biological tissue, an organ slice or part of an organ in vivo or in vitro. For example, the image of the biological structure may be an image of the location of a protein within a cell or tissue or an image of a cell or tissue with endogenous nucleotides (e.g. DNA) to which labeled nucleotide probes bind (e.g. in situ hybridization). The image training data may comprise a pixel value for each pixel of an image for each color dimension of the image (e.g. three color dimensions for RGB representation). For example, depending on the imaging modality other channels may apply related to excitation or emission wavelength, fluorescence lifetime, light polarization, stage position in three spatial dimensions, different imaging angles. The biology-related image-based input training data 104 may be an XY pixel map, volumetric data (XYZ), time series data (XY+T) or combinations thereof (XYZT). Moreover, additional dimensions depending on the kind of image source may be included such as channel (e.g. spectral emission bands), excitation wavelength, stage position, logical position as in a multi-well plate or multi-positioning experiment and/or mirror and/or objective position as in lightsheet imaging. For example, the user may input or a database may provide an image as a pixel map or pictures of higher dimensions. The visual recognition machine-learning algorithm may convert this image into semantic embeddings (e.g. second high-dimensional representation). For example, the biology-related image-based input training data 104 corresponds to the biology-related language-based input training data 102. For example, the biology-related image-based input training data represents a biological structure described by the biology-related language-based input training data 102 so that the biology-related image-based input training data 104 is associated with the biology-related language-based input training data 102. The biology-related image-based input training data 104 may be received from the one or more storage devices, a database stored by a storage device or may be input by a user. The biology-related image-based input training data 104 may be a first biology-related image-based input training data set of a training group. The training group may comprise a plurality of biology-related image-based input training data sets.

A high-dimensional representation (e.g. first and second high-dimensional representation) may be a hidden representation, a latent vector, an embedding, a sematic embedding and/or a token embedding and/or may be also called hidden representation, a latent vector, an embedding, a semantic embedding and/or a token embedding.

The first high-dimensional representation and/or the second high-dimensional representation may be numerical representations (e.g. comprising numerical values only). The first high-dimensional representation and/or the second high-dimensional representation may comprise only positive values or entries with positive values and entries with negative values. In contrast, the biology-related language-based input training data may comprise alphabetic characters or other non-numeric characters only or a mixture of alphabetic characters, other non-numeric characters and/or numerical characters. The first high-dimensional representation and/or the second high-dimensional representation may comprise more than 100 dimensions (or more than 300 dimensions or more than 500 dimensions) and/or less than 10000 dimensions (or less than 3000 dimensions or less than 1000 dimensions). Each entry of a high-dimensional representation may be a dimension of the high-dimensional representation (e.g. a high-dimensional representation with 100 dimensions comprises 100 entries). For example, using high dimensional representations with more than 300 dimensions and less than 1000 dimensions may enable a suitable representation for biology-related data with semantic correlation. The first high-dimensional representation may be a first vector and the second high-dimensional representation may be a second vector. If a vector representation is used for the entries of the first high-dimensional representation and the entries of the second high-dimensional representation, an efficient comparison and/or other calculations (e.g. normalization) may be implemented, although other representations (e.g. as a matrix) may be possible as well. For example, the first high-dimensional representation and/or the second high-dimensional representation may be normalized vectors. The first high-dimensional representation and the second high-dimensional representation may be normalized to the same value (e.g. 1). For example, the last layer of the model (e.g. of the language recognition machine-learning algorithm and/or the visual recognition machine-learning algorithm) may represent a non-linear operation, which may perform the normalization in addition. For example, if the first model (language model) is trained with the cross entropy loss function, a so called SoftMax operation may be used:

$$softmax = \frac{e^{\hat{y}_i}}{\sum_i^K e^{\hat{y}_i}}$$

with $y_i$ being a prediction of the model corresponding to an input value and K being the number of all input values.

For example, the first high-dimensional representation and/or the second high-dimensional representation may comprise various entries (at least three) with values unequal 0 in contrast to one hot encoded representations. By using high-dimensional representations, which are allowed to have various entries with values unequal 0, information on a semantic relationship between the high-dimensional representations can be reproduced. For example, more than 50% (or more than 70% or more than 90%) of values of the entries of the first high-dimensional representation and/or more than 50% (or more than 70% or more than 90%) of values of the entries of the second high-dimensional representation may be unequal 0. Sometimes one hot encoded representations have also more than one entry unequal 0, but there is only one entry with high value and all other entries have values at noise level (e.g. lower than 10% of the one high value). In contrast, the values of more than 5 entries (or more than 20 entries or more than 50 entries) of the first high-dimensional representation may be larger than 10% (or larger than 20% or larger than 30%) of a largest absolute value of the entries of the first high-dimensional representation, for example. Further, the values of more than 5 entries (or more than 20 entries or more than 50 entries) of the second high-dimensional representation may be larger than 10% (or larger than 20% or larger than 30%) of a largest absolute value of the entries of the second high-dimensional representation, for example. For example, each entry of the first high-dimensional representation and/or the second high-dimensional representation may comprise a value between −1 and 1.

The first high-dimensional representation may be generated by an encoder of the language recognition machine-learning algorithm. For example, the first high-dimensional representation is generated by applying the language recognition machine-learning algorithm with a current set of parameters to the biology-related language-based input training data 102. The current set of parameters of the language recognition machine-learning algorithm may be updated during the adjustment of the language recognition machine-learning algorithm. For example, the adjustment of the language recognition machine-learning algorithm comprises an adjustment of a plurality of language recognition neural network weights and a final set of language recognition neural network weights may be stored by the one or more storage devices 120. Further, the second high-dimensional representation may be generated by applying the visual recognition machine-learning algorithm with a current set of parameters to the biology-related image-based input training data. The current set of parameters of the visual recognition machine-learning algorithm may be updated during the adjustment of the visual recognition machine-learning algorithm. For example, the adjustment of the visual recognition machine-learning algorithm comprises an adjustment of a plurality of visual recognition neural network weights and a final set of visual neural network weights may be stored by the one or more storage devices 120.

The values of one or more entries of the first high-dimensional representation and/or the values of one or more entries of the second high-dimensional representation may be proportional to a likelihood of a presence of a specific biological function or a specific biological activity. By using a mapping that generates high-dimensional representations preserving the semantical similarities of the input data sets, semantically similar high-dimensional representations may have a closer distance to each other than semantically less similar high-dimensional representations. Further, if two high-dimensional representations represent input data sets with same or similar specific biological function or specific biological activity one or more entries of these two high-dimensional representations may have same or similar values. Due to the preservation of the semantic, one or more entries of the high-dimensional representations may be an indication of an occurrence or presence of a specific biological function or a specific biological activity. For example, the higher a value of one or more entries of the high-dimensional representation, the higher the likelihood of a presence of a biological function or a biological activity correlated with these one or more entries may be.

The system 100 may repeat generating a first high-dimensional representation for each of a plurality of biology-related language-based input training data sets of a training group. Further, the system 100 may generate biology-related language-based output training data for each generated first high-dimensional representation. The system 100 may adjust the language recognition machine-learning algorithm based on each comparison of biology-related language-based input training data of the plurality of biology-related language-based input training data sets of the training group with the corresponding biology-related language-based output training data. In other words, the system 100 may be configured to repeat generating a first high-dimensional representation, generating biology-related language-based output training data, and adjusting the language recognition machine-learning algorithm for each biology-related language-based input training data of a training group of biology-related language-based input training data sets. The training group may comprise enough biology-related language-based input training data sets so that a training target (e.g. variation of an output of a loss function below a threshold) can be fulfilled.

The plurality of all first high-dimensional representations generated during training of the language recognition machine-learning algorithm may be called latent space or semantic space.

The system 100 may repeat generating a second high-dimensional representation for each of a plurality of biology-related image-based input training data sets of a training group. Further, the system 100 may adjust the visual recognition machine-learning algorithm based on each comparison of a first high-dimensional representation with the corresponding second high-dimensional representation. In other words, the system 100 may repeat generating a second high-dimensional representation and adjusting the visual recognition machine-learning algorithm for each biology-related image-based input training data of a training group of biology-related image-based input training data sets. The training group may comprise enough biology-related image-based input training data sets so that a training target (e.g. variation of an output of a loss function below a threshold) can be fulfilled.

The training group of biology-related language-based input training data sets may comprise more entries than the training group of biology-related image-based input training data sets. For example, if the biology-related language-based input training data sets are different nucleotide sequences or protein sequences, databases with more different nucleotide sequences or protein sequences may be available for training than images of biological structures comprising corresponding nucleotides or corresponding proteins. Further, if the number of trained first high-dimensional representations is larger than the number of trained second high-dimensional representations, zero shot learning of not-trained biology-related image-based input data may be possible. The trained visual recognition machine-learning algorithm may map the unseen biology-related image-based input data to a second high-dimensional representation with low distance to one or more first high-dimensional representations of semantically similar biology-related language-based input data. Alternatively, the training group of biology-related language-based input training data sets may comprise less entries than the training group of biology-related image-based input training data sets, for example, if the biology-related language-based input training data sets are descriptions of different behaviors of biological molecules or biological structures, or descriptions of biological functions or biological activities, since the number of different input data sets for these kinds of input data may be limited (e.g. less than 500, or less than 100 or less than 50 different biology-related language-based input training data sets).

For example, the system 100 uses a combination of a language recognition machine-learning algorithm and a visual recognition machine-learning algorithm (e.g. also called visual-semantic model). The language recognition machine-learning algorithm and/or the visual recognition machine-learning algorithm may be deep learning algorithms and/or artificial intelligence algorithms.

The language recognition machine-learning algorithm may also be called textual model, language model or linguistic model. The language recognition machine-learning algorithm may be or may comprise a language recognition neural network. The language recognition neural network may comprise more than 30 layers (or more than 50 layers or more than 80 layers) and/or less than 500 layers (or less than 300 layers or less than 200 layers). The language recognition neural network may be a recurrent neural network, for example, a long short-term memory network. Using a recurrent neural network, for example a long short-term memory network, may provide a language recognition machine-learning algorithm with high accuracy for biology-related language-based input data. However, also other language recognition algorithms may be applicable. For example, the language recognition machine-learning algorithm may be an algorithm able to handle input data of variable length (e.g. Transformer-XL algorithm). For example, a length of first biology-related language-based input training data of the training group of biology-related language-based input training data sets differs from a length of second biology-related language-based input training data of the training group of biology-related language-based input training data sets. By using an algorithm as the Transformer-XL algorithm, the model may be able to detect structure over, both longer and variable length sequences. The properties specific to Transformer-XL, which may set it apart from other language model architectures using neural networks, may be owed to the ability that semantic dependencies can be learned over variable lengths due to the fact, that the hidden state of each segment, which is being analyzed is reused to obtain the hidden state of the next segment. This kind of state accumulation may allow to build up a recurrent semantic connection between consecutive segments. Thus, long-term dependencies can be captured, which encode biological function. For example, in nucleotide sequences long stretches of DNA get excised (e.g. spliced) during transcription of a gene effectively concatenating nucleotide sequences which had previously been far apart. Using the Transformer-XL architecture may allow to capture those long-term dependencies. Moreover, in protein sequences consecutive secondary polypeptide structures (such as alpha helix or beta sheet) often form so-called "folds" (e.g. three-dimensional arrangements of secondary structure in space). These folds can be part of protein sub-domains each with a unique biological function. So, long-term semantic dependencies may be important to correctly capture the biological function to be encoded in a semantic embedding. Other approaches may be only capable of learning fixed length dependencies, which could limit the model's capability to learn the correct semantics. Protein sequences, for example, typically are tens to hundreds of amino acids long (with one amino acid represented as one letter in the protein sequence). The "semantics", e.g. biological function of substrings from the sequence (called polypeptides, motifs or domains in biology) may vary in length. Thus, using an architecture, such as Transformer-XL, which is capable of adapting to variable length dependencies may be used.

The language recognition machine-learning algorithm may be trained by adjusting parameters of the language recognition machine-learning algorithm based on the comparison of the biology-related language-based input training data 102 and the biology-related language-based output training data. For example, network weights of a language recognition neural network may be adjusted based on the comparison. The adjustment of the parameters (e.g. network weights) of the language recognition machine-learning algorithm may be done under consideration of a loss function (e.g. cross entropy loss function). The loss function may result in a real value being a degree of equivalence between the prediction and the existing annotation. The training may vary the inner degrees of freedom (e.g. the weights of the neural network) until the loss function is minimal. For example, the comparison of the biology-related language-based input training data 102 and the biology-related language-based output training data for the adjustment of the language recognition machine-learning algorithm may be based on a cross entropy loss function. For example, if $M>2$ (e.g. multiclass classification), a separate loss may be calculated for each class label per observation and the result may be summed:

$$-\sum_{c=1}^{M} y_{o,c} \log(p_{o,c})$$

with M being the number of classes (e.g. nucleus, cytoplasm, plasma membrane, mitochondria in the case of cell organelles), log being the natural logarithm, y being a binary indicator (0 or 1), if class label c is the correct classification for observation o, and p being the predicted probability for observation o is of class c.

The training may converge fast and/or may provide a well-trained algorithm for biology-related data by using the cross entropy loss function for training the language recognition machine-learning algorithm, although other loss functions could be used as well.

The visual recognition machine-learning algorithm may also be called image recognition model, visual model or image classifier. The visual recognition machine-learning algorithm may be or may comprise a visual recognition neural network. The visual recognition neural network may comprise more than 20 layers (or more than 40 layers or more than 80 layers) and/or less than 400 layers (or less than 200 layers or less than 150 layers). The visual recognition neural network may be a convolutional neural network or a capsule network. Using a convolutional neural network or a capsule network may provide a visual recognition machine-learning algorithm with high accuracy for biology-related image-based input data. However, also other visual recognition algorithms may be applicable. For example, the visual recognition neural network may comprise a plurality of convolution layers and a plurality of pooling layers. However, pooling layers may be avoided, if a capsule network is used and/or stride=2 is used instead of stride=1 for the convolution, for example. The visual recognition neural network may use a rectified linear unit activation function. Using a rectified linear unit activation function may provide a visual recognition machine-learning algorithm with high accuracy for biology-related image-based input data, although other activation functions (e.g. a hard tan h activation function, a sigmoid activation function or a tan h activation function) may be applicable as well.

For example, the visual recognition neural network may comprise a convolutional neural network architecture and/or may be a ResNet or a DenseNet of a depth depending on the size of the input images. For example, up to an image pixel size of 384×384 pixels a ResNet architecture up to depth of 50 layers may provide good results. From ~512×512 to 800×800 pixels a ResNet with depth 101 layers may be used. Above these image sizes deeper architectures may be used, such as ResNet151 or DenseNet121 or DenseNet169.

The visual recognition machine-learning algorithm may be trained by adjusting parameters of the visual recognition machine-learning algorithm based on the comparison of a high dimensional representation generated by the language recognition machine-learning algorithm with a high dimensional representation generated by the visual recognition machine-learning algorithm of corresponding input training data. For example, network weights of a visual recognition neural network may be adjusted based on the comparison. The adjustment of the parameters (e.g. network weights) of the visual recognition machine-learning algorithm may be done under consideration of a loss function. For example, the comparison of the first high-dimensional representation and the second high-dimensional representation for the adjustment of the visual recognition machine-learning algorithm may be based on a cosine similarity loss function. The training may converge fast and/or may provide a well-trained algorithm for biology-related data by using the cosine similarity loss function for training the visual recognition machine-learning algorithm, although other loss functions could be used as well.

For example, the visual model may learn how to represent an image in the semantic embedding space (e.g. as a vector). So, a measure for the distance of two vectors may be used, which may represent the prediction A (the second high-dimensional representation) and the ground-truth B (the first high-dimensional representation). For example, a measure is the cosine similarity as defined in $$\text{similarity} = \cos(\theta) = \frac{A \cdot B}{\|A\|\|B\|}$$

with the dot product of the prediction A and ground-truth B divided by the dot product of their respective magnitudes (e.g. as in L2-Norm or Euclidian norm).

Figure 2:
FIG. 2 is a schematic illustration of a training of a language recognition machine-learning algorithm.
Figure 2:
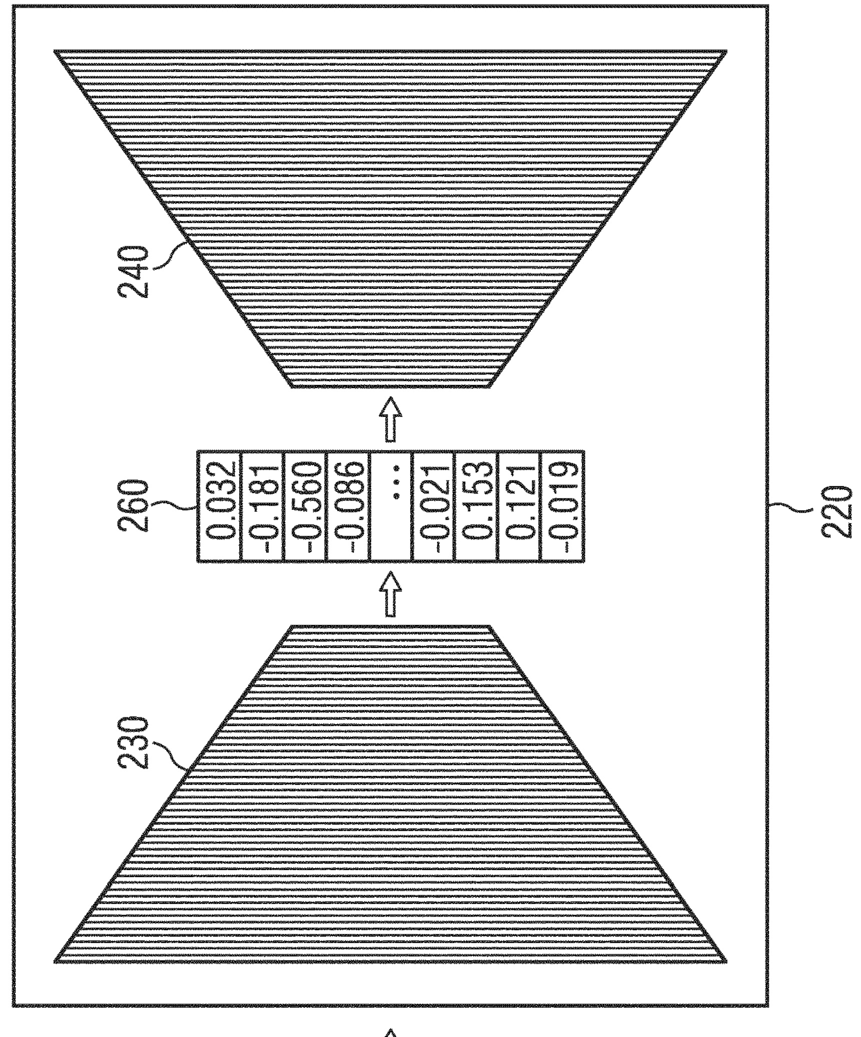

FIG. 2 shows an example of a training of the language recognition machine-learning algorithm 220 (e.g. illustrating the finding of token embeddings). A textual model 220 may be trained on biological sequences or natural language 210 (e.g. a nucleotide sequence, for example, GATTACA) coming from a database 200 or an imaging device (e.g. a microscope) in a running experiment. A natural language processing (NLP) task is, for example, to predict the next word (dependent variable) in a sentence (independent variable) or to predict the next character given a short stretch of text 250 (e.g. the next nucleotide in the nucleotide sequence, for example, C following GATTACA). Other NLP tasks can involve predicting sentiment from a text or translation. In the context of biological sequences the independent variables may be protein sequences or nucleotide sequences or short stretches thereof. The dependent variables can be the next element in the sequence or any of the mentioned coarse-grained search terms or combinations thereof. During training the data may be passed down an encoder path 230 to learn a hidden representation 260 (first high-dimensional representation) and up through a decoder path 240 to make a useful prediction 250 (e.g. biology-related language-based output training data) from it. A quantitative metric (e.g. loss function) may measure the accuracy of the prediction relative to ground truth data. The gradient of this loss function with respect to the model's trainable parameters may be used to adjust these trainable parameters. This training may be iterated until a preset threshold for the loss function is met. The result of finding token embeddings during training may be a mapping from each token to its respective embedding, e.g. latent vector 260 (first high-dimensional representation). The latent space may represent a semantic space. For example, a meaning may be assigned to each token (e.g. word or peptide or polynucleotide) by this embedding.

The prediction 250 may be represented by the biology-related language-based output training data y. For example, y=W*X with X being the biology-related language-based input training data (e.g. biological sequence) and W the trained parameters of the model. In addition, a bias term may be included.

Optionally, images may be mapped to token embeddings after training the language recognition machine-learning algorithm. In other words, images may be selected showing a biological structure corresponding to the biology-related language-based input training data. For example, the biology-related language-based input training data may be a nucleotide sequence (e.g. GATTACA in FIG. 2) and an image of a biological structure comprising this nucleotide sequence may be selected. A plurality of images corresponding to a plurality of biology-related language-based input training data sets may be selected as training set for training the visual recognition machine-learning algorithm. The selection of training images might be avoided, if a database of such training images is already available.

The visual model may be charged with a computer vision task, such as predicting the class(es) of an image, for example, which subcellular compartment is shown in the image. In other applications, a visual model gets one-hot encoded labels as dependent variables. For example, the system 100 maps the image classes to the respective token embeddings learned by the textual model as described above. For example, an image classifier which learns to predict the classes "p53", "Histone H1" and "GAPDH" would learn to predict the token embeddings of the respective protein sequences for the three proteins (e.g. same may apply to token embeddings learned from nucleotide sequences or textual descriptions in scientific publications). The mapping itself in the ground truth data may be a look-up table of pictures showing the molecule of interest and its respective semantic embedding of the biological sequence or natural language used for training.

Only the high-dimensional representations 260 may be of interest, which may be obtained by a forward pass of an input text through the language recognition machine-learning algorithm. For the training, a language classification problem may be defined. For example, a soft max layer may follow the determination of the high-dimensional representations 260 and the cross entropy loss function may be used for training. In FIG. 2 an additional decoder path 240 is shown, which generates again a text, which represents the case when the model outputs a text. For example, the prediction of a second half of a sentence may be done, if the first words are input. For a biology-related application, for example, the first part of a sequence may be input and the second half or only the next character of the sequence may be predicted with a specific probability. This prediction 250 might not be of interest as only the high-dimensional representations 260 are of interest, but the prediction may improve the training. The visual model of FIG. 3 may then predict the high-dimensional representation 260 as ground truth 330. For this application, a cosine distance function may be used as loss function instead of a cross entropy loss function. Both vectors 260, 330 might not be normalized to 0 or 1. As BatchNormalization may be used to keep the numbers controllable, the values of a vector might not be far larger than 1.

Figure 3:
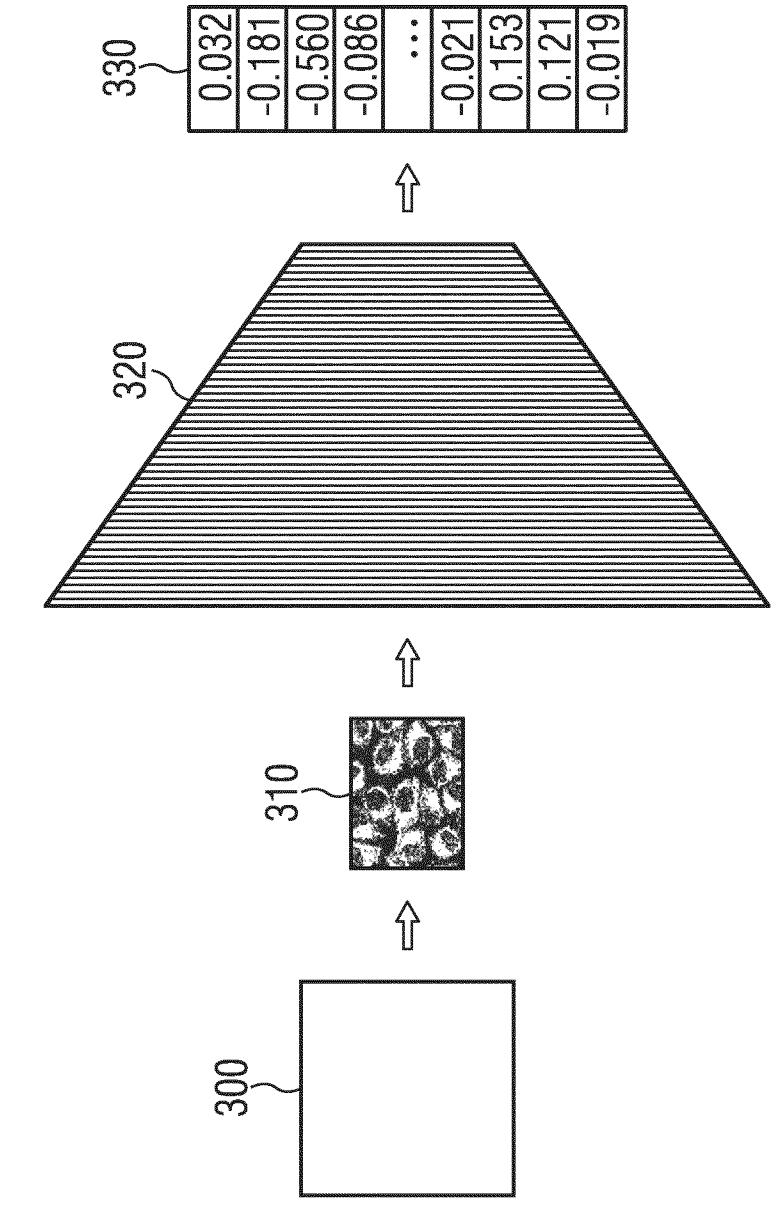
FIG. 3 is a schematic illustration of a training of a visual recognition machine-learning algorithm.

FIG. 3 shows an example of a training of the visual recognition machine-learning algorithm 320. The training of the visual model 320 may be performed to predict token embeddings. As shown in FIG. 3, a visual model 320 may be trained on images 310 from a data repository 300, such as a public or private image database, or a microscope in a running experiment. The dependent variables may be the corresponding token embeddings 330 (second high-dimensional representation) learned by a textual model and optionally mapped to image classes as described above. The visual model may learn to predict a representation of the image classes which contain the semantics of biological function learned by a textual model in the preceding training stage.

FIG. 4 shows an example of a part 400 (e.g. ResNet block) of a visual recognition neural network based on a ResNet architecture. For example, the visual recognition neural network may be described with the following parameters (e.g. similar to a ResNet). The dimensions of a tensor (e.g. data passed through deep neural network) may be:

$$\text{shape} = bs \times ch \times \text{height} \times \text{width}$$

with bs being the batch size (e.g. number of images loaded into one mini-batch of stochastic gradient descent optimization), ch being the number of filters (e.g. equivalent to the number of "channels" for the input images, for example ch=3 for RGB images), height being the number of rows in the image, and width being the number of columns in the image. For example, a microscope may be capable of producing more dimensions (e.g. an axial dimension (z), spectral emission dimensions, lifetime dimensions, spectral excitation dimensions and/or stage dimensions), which may be processed by the visual recognition neural network in addition. However, the following example may relate only to the case with channels, height and width (e.g. examples with ch>3 may be implemented as well).

The visual recognition neural network may be represented as computational graph and operations may be summarized as "layers" representing specific operations on the input data (e.g. a tensor). The following notations may be used:

ch_0 Number of channels of input tensor before operations.

| | |
|---|---|
| ch_0 | Number of channels of input tensor before operations. |
| X | X may be an n-dimensional tensor of the shape as defined above |
| conv($n_{in}$, $n_{out}$, k, s) (x) | n-dimensional convolution operation 430 (e.g. in the case shown here 2D convolution) with n_in input channels (e.g. spatial filters), n_out output channels, kernel size k by k (e.g. 3 × 3), stride s by s (e.g. 1 × 1) applied to tensor X. |
| $\text{relu}(x) = \begin{cases} 0 \text{ if } x < 0 \\ x \text{ otherwise} \end{cases}$ | Rectified linear unit is a non-linearity executed after convolution as shown. In the graph this operation is depicted as "Relu" 420. |
| $\text{bn}(x) = \frac{x - \mu}{\sigma}$ | Batch normalization gets Tensor X normalized to its respective batch's mean u and standard deviation o. In the graph this operation is depicted as "BatchNormalization" 410. |
| fc(x) = Wx + b | Fully connected layer is a linear operator with W being the weights and b the bias term (e.g. b is not shown in the graphs). $W \in \mathbb{R}^{bs \times ch \times n\_in \times n\_out}$ with n in and n out being the input and output channel dimensions of the current activation. |
| rn(x) | ResNet block 400 with bottleneck configuration applied to tensor X of shape (1,64, 256, 256) starting with the activations from the previous layer is shown in FIG. 4. |

Some Bottleneck blocks may downsample the spatial dimension by a factor of 2 while upsampling the number of channels (e.g. spatial filters) by 4. ResNet blocks may be combined in groups to yield overall architectures of 18 through 152 layers. For example, using 50, 101 or 152 layers and bottleneck resnet blocks and/or a ResNet block with pre-activation may be used for the visual recognition neural network of the proposed concept.

For example, the visual recognition neural network may comprise at least a first batch normalization operation 410 followed by a first ReLu operation 420 followed by a first convolution operation 430 (e.g. 1×1) followed by a second batch normalization operation 410 followed by a second ReLu operation 420 followed by a second convolution operation 430 (e.g. 3×3) and followed by an adding operation 440 (e.g. adding the output of the second convolution operation and the input of the first batch normalization operation). One or more additional operations may be performed before the first batch normalization operation 410, after the adding operation 440 and/or in between.

FIG. 5 shows an example of a part 500 (e.g. a modified ResNet-Convolutional Block Attention Module CBAM block) of a visual recognition neural network 400 based on a ResNet architecture. For example, a ResNet-CBAM block 500 may use a so-called Channel Attention block in a ResNet block combined with spatial attention.

The following notations may be used in addition to the notations used in conjunction with FIG. 4:

$$gap(x) = \frac{1}{h \times w} \sum_{i=1}^{h} \sum_{j=1}^{w} x(i, j)$$

Global average pooling collapses a tensor X with dimensions (bs×ch×h×w) to dimensions (bs×ch×1×1) by averaging over height and width dimensions. In the graph this operation is depicted as "GlobalAveragePool" 510.

$$gmp(x) = \max_{i=0, \ldots, h} \max_{j=0, \ldots, w} x(i, j)$$

Global maximum pooling collapses a tensor X with dimensions (bs×ch×h×w) to dimensions (bs×ch×1×1) by selecting the maximum over height and width dimensions. In the graph this operation is depicted as "GlobalMaxPool" 520.

For channel attention, a concatenation 530 of GlobalAveragePooling 510 and Global-MaxPooling 520 may be used instead of GlobalAveragePooling 510 alone. In this way, the model may learn both, a "soft" global average pooling making the model more resilient to outliers while preserving the maximal activation. So, the model may be able to decide which one to emphasize. For example, the output of a previous operation may be provided as input for the GlobalAveragePooling operation 510 and the Global-MaxPooling operation 520 and the output of the GlobalAveragePooling operation 510 and the output of the Global-MaxPooling operation 520 may be provided as input to the same following operation (e.g. concatenation).

Further, a 1×1 kernel size may be used instead of a mini MLP (multi layer perceptron), which may save somewhat redundant flattening and unsqueezing operations in the channel attention module.

Both, the channel attention module and the spatial attention module may use a sigmoid non-linearity 540 as the last activation function. In this way, a more favorable feature scaling may be obtained than with the ReLU activation.

Optionally, in between the channel attention and the spatial attention, a batch normalization 410 may be performed just after the scaling with channel attention has occurred to avoid gradients from becoming excessively large.

The output of the preceding ResNet Bottleneck block and the CBAM block are added as shown in FIG. 5. The CBAM block starts with "GlobalAverage-Pooling" 510 and "Global-MaxPooling" 520 and ends with the last "Mul" (Multiplication) 550.

From these Rn_CBAM(x) building blocks, a ResNet architecture may be constructed by replacing the $$\begin{pmatrix} 1 \times 1 \\ 3 \times 3 \\ 1 \times 1 \end{pmatrix}_{add}$$

bottleneck blocks by the Rn_CBAM(x) shown in FIG. 5. For example, deeper architectures with 50, 101 and 152 layers may be used for the proposed concept, although other depths may be possible as well.

The Mean operation 560 and the Max operation 570 may work together by generating an arithmetic mean over the dimensions ch through the Mean operation 560 (e.g. so 1×64×256×256 gets 1×1×256×256) and a maximum projection along the dimensions ch through the Max operation 570. The following concatenation operation 530 concatenates the result of the two projections.

For example, the visual recognition neural network may comprise at least a first batch normalization operation 410 followed by a first ReLu operation 420 followed by a first convolution operation 430 (e.g. kernel size 1×1) followed by a second batch normalization operation 410 followed by a second ReLu operation 420 followed by a second convolution operation 430 (e.g. kernel size 3×3) followed by a GlobalAveragePooling operation 510 in parallel to a Global-MaxPooling operation 520 followed by a first concatenation operation 530 followed by a third convolution operation 430 (e.g. 1×1) followed by a third ReLu operation 420 followed by a fourth convolution operation 430 (e.g. kernel size 1×1) followed by a first sigmoid operation 540 followed by a first multiplication (Mul) operation 550 (e.g. multiplying the output of the first sigmoid operation and the output of the second convolution operation) followed by a third batch normalization operation 410 followed by a Mean operation 560 in parallel to a Max operation 570 followed by a second concatenation operation 530 followed by a fifth convolution operation 430 (e.g. kernel size 7×7) followed by a second sigmoid operation 540 followed by a second multiplication (Mul) operation 550 (e.g. multiplying the output of the second sigmoid operation and the output of the third batch normalization operation) and followed by an adding operation 440 (e.g. adding the output of the second multiplication operation and the input from the previous block). The operations between the second convolution operation and the third batch normalization operation may be called channel attention module and the operations between the first multiplication operation and the second multiplication operation may be called spatial attention module. The operations from the first batch normalization operation to the second convolution operation may be called ResNet Bottleneck block and the operations between the second convolution operation and the second multiplication operation may be called CBAM block. The CBAM block may be used to scale the second convolution so that the model focuses on the correct features. One or more additional operations may be performed before the first batch normalization operation 410, after the adding operation 440 and/or in between.

FIG. 6 shows an example of a part 600 (e.g. dense layer with bottleneck configuration) of a visual recognition neural network based on a DenseNet architecture. An alternative architecture to ResNet is called DenseNet, which relies on concatenating successive activation maps (e.g. instead of adding as in ResNet) to make activations of upstream layers directly available to downstream layers. For the proposed concept, a DenseNet architecture with added attention mechanism on the level of individual dense layers Hl_B(x) may be used. A channel attention mechanism may be combined with sparsified DenseNets.

For the proposed concept, both, spatial and channel attention may be combined with dense layers. Optionally, batch normalization between the channel and spatial attention modules may be used as described with the ResNet architecture (e.g. in conjunction with FIGS. 4 and 5). Instead of adding the output of the attention path to the output of the dense layer, only the attention mechanism may be applied to the k activations newly generated by the dense layer and the resealed output of the attention path may be concatenated to the input of the dense layer at the end. For example, for all but the very first dense layer the activations have already gone through a previous dense layer with attention mechanism attached. Re-scaling successively might not further improve the result. Conversely, such re-scaling might even prevent the network from learning new attentional rescalings in more down-stream layers as needed. Further, applying attention only to the k newly created layers may reduce computational complexity and may omit the need for a reduction ratio r as a patch to cap computational complexity. For the dense layer and DenseNet block, the full configuration may be used rather than a sparse configuration.

The following notations may be used in addition to the notations used in conjunction with FIGS. 4 and 5:

Hl_B(x) Dense layer 600 with bottleneck configuration is shown in FIG. 6.

$$\begin{pmatrix} 1\times 1 \\ 3\times 3 \end{pmatrix}_{concat}$$

The input tensor X with dimensions (bs, ch, h, w) is passed through two successive convolutions with pre-activation (bn+relu) each. The first convolution has a 1×1 kernel and outputs ch number of activations. The second convolution has a 3×3 kernel and outputs only k activations. In this example k=16. At the end the 16 new activations are concatenated with the input of the dense layer. In this example ch=64, so the output has ch+k=80 activations.

In comparison to the part of a visual recognition neural network shown in FIG. 4, the adding operation 440 is replaced by a concatenation operation 530 (e.g. of the output of the second convolution operation and the input of the first batch normalization operation). More details are described in conjunction with FIG. 4.

Figures 1, 2, 7:
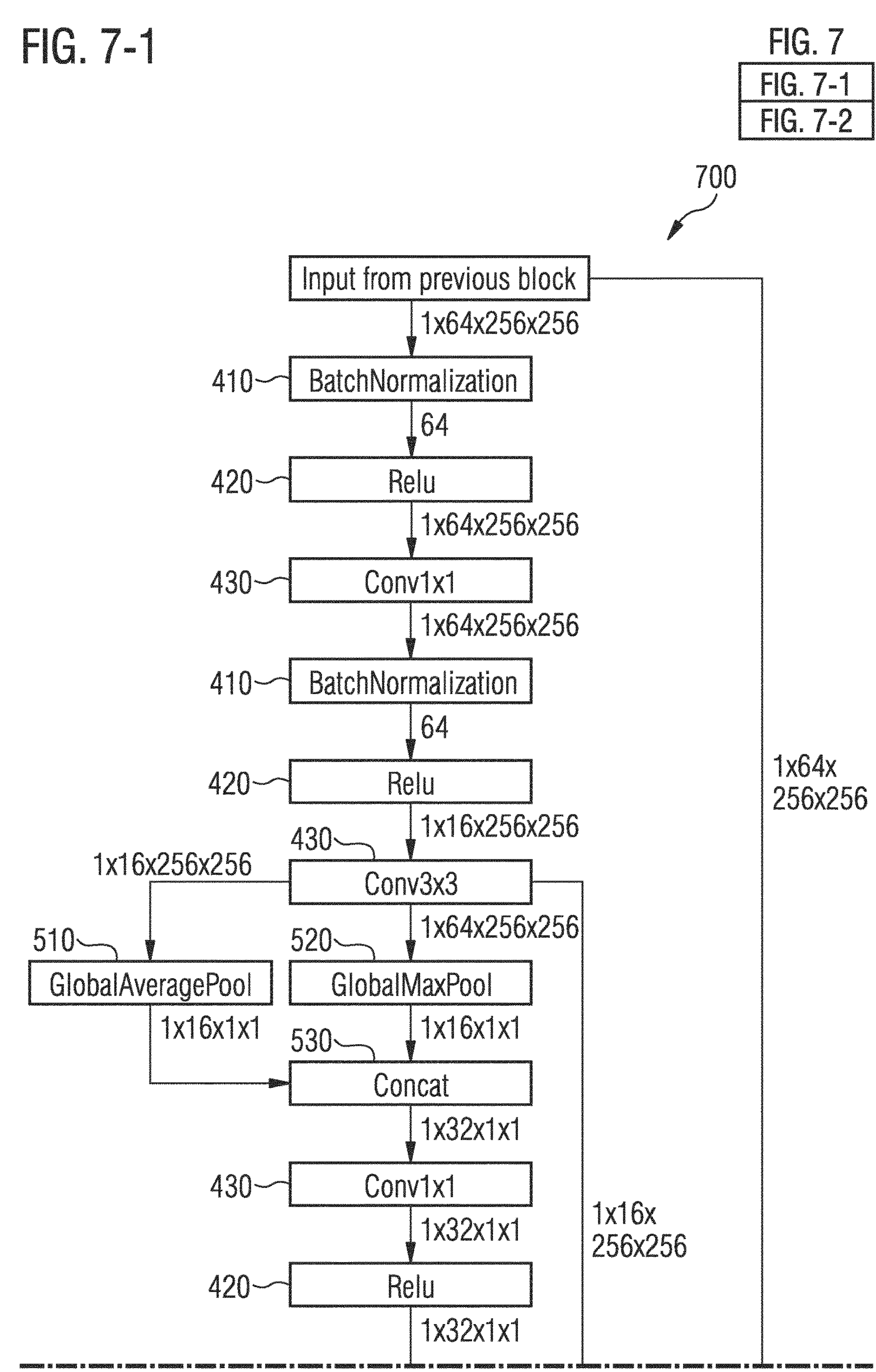
FIG. 7 is a computational graph of a part of a visual recognition neural network based on a DenseNet architecture with attention mechanism.
Figures 2, 7:
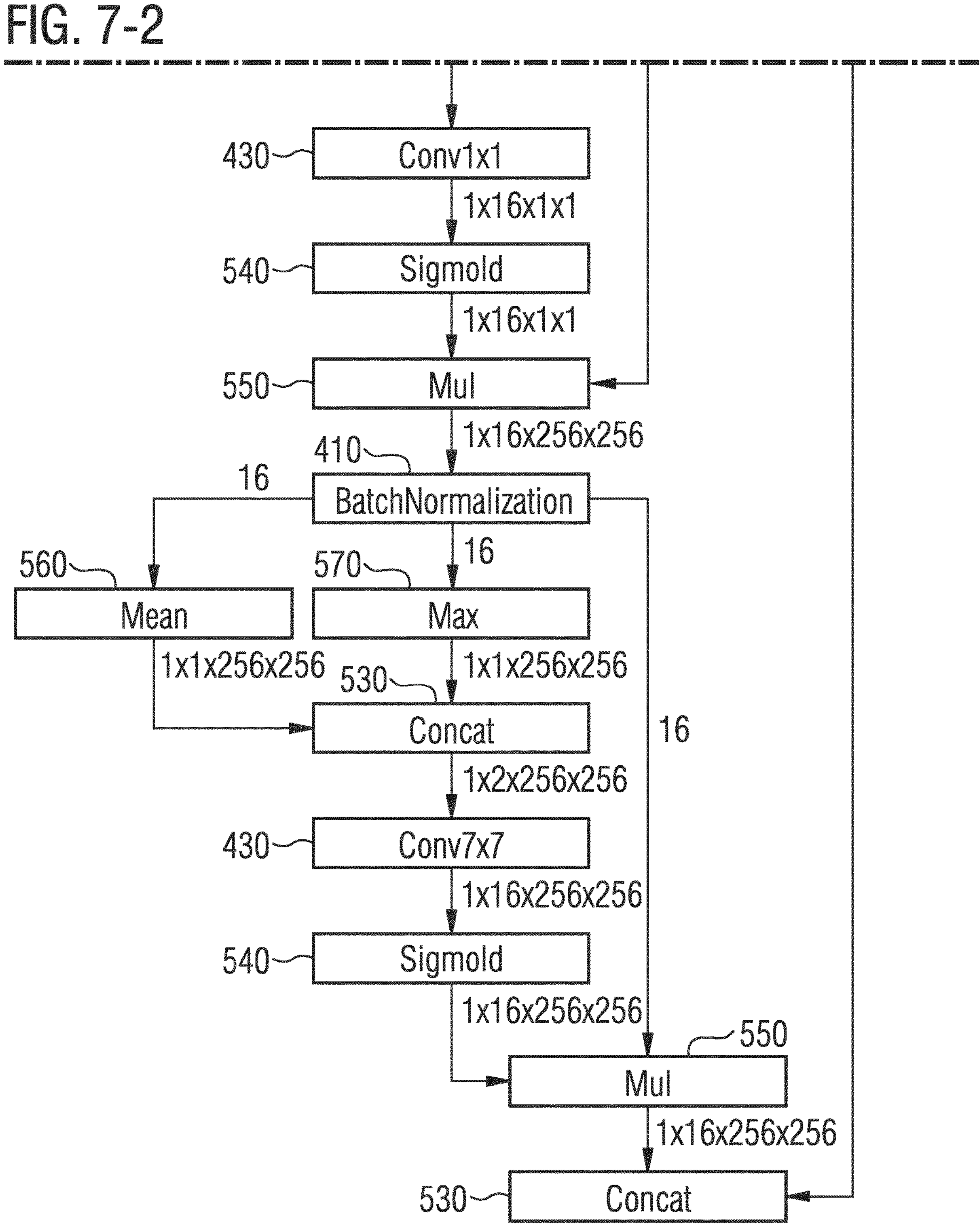

FIG. 7 shows an example of a part 700 (e.g. dense layer with attention mechanism) of a visual recognition neural network based on a DenseNet architecture.

The following notations may be used in addition to the notations used in conjunction with FIGS. 4, 5 and 6:

Hl_A Dense layer 700 with attention mechanism.

$$\begin{pmatrix} 1\times 1 \\ 3\times 3 \end{pmatrix}_{concat,attention}$$

This building block of the DenseNet may be used for the proposed concept. Similar to the attention mechanism described for the ResNet above, two successive attention modules are introduced with channel and spatial attention respectively. The output of the attention path is concatenated with the output of the dense layer.

From these Hl_A(x) building blocks, a DenseNet may be obtained by replacing the $$\begin{pmatrix} 1\times 1 \\ 3\times 3 \end{pmatrix}_{concat}$$

elements by their respective Hl_A(x) counterparts.

In comparison to the part of a visual recognition neural network shown in FIG. 5, the adding operation 440 is replaced by a concatenation operation 530 (e.g. of the output of the second multiplication operation and the input of the first batch normalization operation). More details are described in conjunction with FIG. 5.

The system 100 may be configured to use a visual recognition neural network comprising a part as shown in one of the FIG. 4-7.

The system 100 may comprise or may be a computer device (e.g. personal computer, laptop, tablet computer or mobile phone) with the one or more processors 110 and one or more storage devices 120 located in the computer device or the system 100 may be a distributed computing system (e.g. cloud computing system with the one or more processors 110 and one or more storage devices 120 distributed at various locations, for example, at a local client and one or more remote server farms and/or data centers). The system 100 may comprise a data processing system that includes a system bus to couple the various components of the system 100. The system bus may provide communication links among the various components of the system 100 and may be implemented as a single bus, as a combination of busses, or in any other suitable manner. An electronic assembly may be coupled to the system bus. The electronic assembly may include any circuit or combination of circuits. In one embodiment, the electronic assembly includes a processor which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA) of the microscope or a microscope component (e.g. camera) or any other type of processor or processing circuit. Other types of circuits that may be included in electronic assembly may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The system 100 includes one or more storage devices 120, which in turn may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The system 100 may also include a display device, one or more speakers, and a keyboard and/or controller, which can include a mouse, trackball, touch screen, voice-recognition device, or any other device that permits a system user to input information into and receive information from the system 100.

Additionally, the system 100 may comprise a microscope connected to a computer device or a distributed computing system. The microscope may be configured to generate the biology-related image-based input training data 104 by taking an image from a biological specimen.

The microscope may be a light microscope (e.g. diffraction limited or sub-diffraction limit microscope as, for example, a super-resolution microscope or nanoscope). The microscope may be a stand-alone microscope or a microscope system with attached components (e.g. confocal scanners, additional cameras, lasers, climate chambers, automated loading mechanisms, liquid handling systems, optical components attached, like additional multiphoton light paths, lightsheet imaging, optical tweezers and more). Other image sources may be used as well as long as they can take images of objects which are related to biological sequences (e.g. proteins, nucleic acids, lipids). For example, a microscope according to an embodiment described above or below may enable deep discovery microscopy.

More details and aspects of the system 100 are mentioned in conjunction with the proposed concept and/or the one or more examples described above or below (e.g. FIGS. 8-9). The system 100 may comprise one or more additional optional features corresponding to one or more aspects of the proposed concept and/or of one or more examples described above or below.

Some embodiments relate to a microscope comprising a system as described in conjunction with one or more of the FIGS. 1-7. Alternatively, a microscope may be part of a system as described in conjunction with one or more of the FIGS. 1-7. FIG. 8 shows a schematic illustration of a system 800 for training machine-learning algorithms. A microscope 810 configured to take images of biological specimens is connected to a computer device 820 (e.g. personal computer, laptop, tablet computer or mobile phone) configured to train a machine-learning algorithm. The microscope 810 and the computer device 820 may be implemented as described in conjunction with one or more of the FIGS. 1-7.

Figures 8, 9:
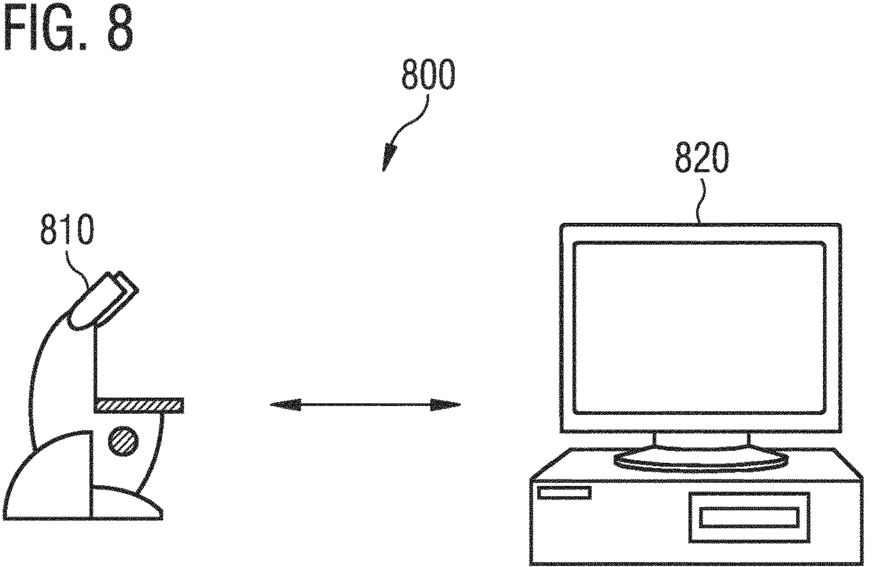
FIG. 8 is a schematic illustration of a system for training machine-learning algorithms for processing biology-related data.
FIG. 9 is a flow chart of a method for training machine-learning algorithms for processing biology-related data.

FIG. 9 shows a flow chart of a method for training machine-learning algorithms for processing biology-related data. The method 900 comprises receiving 910 biology-related language-based input training data and generating 920 a first high-dimensional representation of the biology-related language-based input training data by a language recognition machine-learning algorithm. The first high-dimensional representation comprises at least three entries each having a different value. Further, the method 900 comprises generating 930 biology-related language-based output training data based on the first high-dimensional representation by the language recognition machine-learning algorithm and adjusting 940 the language recognition machine-learning algorithm based on a comparison of the biology-related language-based input training data and the biology-related language-based output training data. Additionally, the method 900 comprises receiving 950 biology-related image-based input training data associated with the biology-related language-based input training data and generating 960 a second high-dimensional representation of the biology-related image-based input training data by a visual recognition machine-learning algorithm. The second high-dimensional representation comprises at least three entries each having a different value. Additionally, the method 900 comprises adjusting 970 the visual recognition machine-learning algorithm based on a comparison of the first high-dimensional representation and the second high-dimensional representation.

By using a language recognition machine-learning algorithm textual biological input can be mapped to a high-dimensional representation. By allowing the high-dimensional representation to have entries with various different values (in contrast to one hot encoded representations), semantically similar biological inputs can be mapped to similar high-dimensional representations. By training a visual recognition machine-learning algorithm to map images to the high-dimensional representations trained by the language recognition machine-learning algorithm, images with similar biological content can be mapped to similar high-dimensional representations as well. Consequently, the likelihood of a semantically correct or at least semantically close classification of images by a correspondingly trained visual recognition machine-learning algorithm may be significantly improved. Further, it may be possible for the correspondingly trained visual recognition machine-learning algorithm to map untrained images more accurately to a high-dimensional representation close to high-dimensional representation of similar meaning or to a semantically matching high-dimensional representation. A trained language recognition machine-learning algorithm and/or a trained visual recognition machine-learning algorithm may be obtained by the proposed concept, which may be able to provide a semantically correct or very accurate classification of biology-related language based and/or image-based input data. The trained language recognition machine-learning algorithm and/or the trained visual recognition machine-learning algorithm may enable a search of biology-related images among a plurality of biological images based on a language-based search input or an image-based search input, tagging of biology-related images, finding or generating typical images and/or similar applications.

More details and aspects of method 900 are mentioned in conjunction with the proposed concept and/or the one or more examples described above or below (e.g. FIGS. 1-8). The method 900 may comprise one or more additional optional features corresponding to one or more aspects of the proposed concept and/or of one or more examples described above or below.

Some embodiments relate to a trained machine learning algorithm trained by receiving biology-related language-based input training data and generating a first high-dimensional representation of the biology-related language-based input training data by a language recognition machine-learning algorithm. The first high-dimensional representation comprises at least 3 entries each having a different value. Further, the trained machine learning algorithm was trained by generating biology-related language-based output training data based on the first high-dimensional representation by the language recognition machine-learning algorithm and adjusting the language recognition machine-learning algorithm based on a comparison of the biology-related language-based input training data and the biology-related language-based output training data. Additionally, the trained machine learning algorithm was trained by receiving biology-related image-based input training data associated with the biology-related language-based input training data and generating a second high-dimensional representation of the biology-related image-based input training data by a visual recognition machine-learning algorithm, wherein the second high-dimensional representation comprises at least 3 entries each having a different value. Further, the trained machine learning algorithm was trained by adjusting the visual recognition machine-learning algorithm based on a comparison of the first high-dimensional representation and the second high-dimensional representation.

The trained machine learning algorithm may be a trained visual recognition machine-learning algorithm (e.g. the adjusted visual recognition machine-learning algorithm) and/or a trained language recognition machine-learning algorithm (e.g. the adjusted language recognition machine-learning algorithm). At least a part of the trained machine learning algorithm may be learned parameters (e.g. neural network weights) stored by a storage device.

More details and aspects of trained machine learning algorithm are mentioned in conjunction with the proposed concept and/or the one or more examples described above or below (e.g. FIGS. 1-9). The trained machine learning algorithm may comprise one or more additional optional features corresponding to one or more aspects of the proposed concept and/or of one or more examples described above or below.

In the following, some examples of applications and/or implementation details for one or more of the embodiments described above (e.g. in conjunction with one or more of the FIGS. 1-9) are described.

For example, biology in general and microscopy in particular are generating vast amounts of data, which often gets poorly annotated or not annotated at all. Often it only becomes apparent in retrospect which annotations might have been useful or new biological discoveries are made not known at the time of the experiment. Based on the proposed concept, such data may be made accessible by allowing semantic searching and tagging of large bodies of image data stored in a database or as part of a running experiment in a microscope. The experiment may be a single one-time experiment or part of a long-term experiment such as a screening campaign.

In the context of a running experiment the proposed concept can help to automate searching biological structures which are part of a specimen, such as proteins expressed in single cells, organoids or tissues, but also more general structures such as organs or developmental states. In this way, the automation of a time-consuming step of finding the relevant parts within a specimen may be enabled. Otherwise this step may require a human expert doing repetitive manual work in an uncomfortable environment (e.g. noisy dark room) under time pressure (e.g. because a costly research instrument was booked for some time). The proposed concept may also make this step more objective by avoiding individual bias.

The proposed concept may enable zero-shot learning, meaning the classification or annotation of images of a type never seen before. Because the image model part of the proposed concept may predict semantic embeddings (e.g. high dimensional representations) rather than one-hot encoded classes, the proposed concept may be capable of finding the closest match for an unknown image in semantic space (e.g. plurality of high dimensional representations). For example, it may be possible to make new discoveries finding previously unknown biological functions in microscopic structures. For example, if there is no matching information to be found in the database the proposed concept may infer the missing information based on the image or the available information. This may enable searching of large bodies of existing data with none or poor annotations.

The proposed concept may use a deep learning approach which combines semantic text embeddings with an image model (e.g. a convolutional neural network, CNN) to make non-annotated or poorly annotated biological images, image stacks, time lapses or combinations thereof such as from light or electron microscopy searchable or extracts biological information from them. According to an aspect a combination of textual and visual models (e.g. language recognition and visual recognition algorithms) may be used in microscopy.

The proposed visual-semantic model (e.g. combination of a language recognition machine-learning algorithm and a visual recognition machine-learning algorithm) may be based on a two-stage process. Stage 1 may train a textual model (e.g. language recognition algorithm) on biological sequences to solve a text cognition task. The semantic embeddings found by the stage 1 model may then be used as a target value to be predicted by a visual model (e.g. visual recognition algorithm) in stage 2. This combination as well as the application in a microscope, optionally during a running experiment may allow various applications.

For example, one-hot encoded class vectors, which other visual models are trained for classification tasks, treat each class as completely unrelated, thus failing to capture any semantics of the class. In contrast, the stage 1 textual model may capture semantics as token embeddings (e.g. also called latent vectors, semantic embeddings or high dimensional representations). Tokens may be characters, words, or in the context of biomolecules, secondary structures, binding motifs, catalytic sites, promotor sequences and others. The visual model may then get trained on these semantic embeddings and can thus make predictions not only on the same classes it was trained on, but also on new classes not contained in the training set. The semantic embedding space thus may serve as a proxy of biological function. Molecules with similar functions imaged by a proposed imaging system (e.g. microscope) may appear as adjacent in this embedding space. In contrast, with other classifiers predicting one-hot encoded class vectors information about biological function is not available. Therefore, other classifiers fail at making predictions on previously unseen classes ("zero-shot learning") and if they misclassify, the predicted class is often completely unrelated to the actual one.

The proposed concept may train a predictive model, as in deep neural network, by combining a textual model (e.g. language model) which gets trained on text and learns semantic embeddings as the hidden representation of the text. Biological sequences such as protein sequences or nucleotide sequences may be used as text. Other embodiments may use natural language such as text used in scientific publications to describe the function of a biomolecule. A visual model (e.g. convolutional neural network, CNN) may get trained to predict their respective embeddings (e.g. unlike one-hot encoded feature vectors used otherwise).

For example, an aspect of the proposed concept describes systems and embodiments built upon the combination of language models (or textual model) and visual models.

The language model may be carried out as deep recurrent neural network (RNN) such as long short-term memory (LSTM) models. The visual model may be carried out as a deep convolutional neural network (CNN). Other embodiments might use different types of deep learning or machine learning models. For example, a visual model may be carried out as a capsule network.

The combination of textual and visual information across different knowledge domains may allow the visual model to learn truly semantic representations of the images it was trained with. For example, in the field of image classification a CNN may get trained to predict different classes describing the image content in one word. This word gets represented as a one-hot encoded vector. In a one-hot encoding the encodings for "*Lilium* sp. pollen grain" and "Endosomes" are as close or as far apart as "Endosomes" and "Lysosomes", even though the two cell organelles are much more similar to one another than cell organelles and pollen grains. So, a visual model which was trained to predict a one-hot encoded vector may be either fully right or fully wrong.

However, if a model gets trained to predict a semantic embedding (e.g. learned by a language model) of the class, its prediction may be closer to semantically related objects in this embedding space.

For example, according to the proposed concept the language model gets trained on text and learns semantic embeddings as a hidden representation of the text. For example, a language model which was trained to predict the next word in a sentence may represent a word in a 500-dimensional latent vector. Other dimensionalities are possible as well. Latent vectors between 50 and 1000 dimensions may be used in natural language processing. The proposed concept may use biological sequences such as protein sequences or nucleotide sequences as text and train a visual model to predict their respective embeddings. A biological sequence may encode a biological function and thus may be understood as a form of "biological language". In addition, also natural language can be used to represent images, because there are large bodies of scientific publications which describe the functional roles of biological entities such as proteins or nucleotide sequences, but also the subcellular localization or developmental and/or metabolic state which makes this information useful in characterizing microscopy images.

The steps towards obtaining a trained model may be, for example:

- Finding token embeddings: Training of a first language/linguistic model (e.g. RNN, LSTM) based on representations of a biological molecule, for example, in form of nucleotide/protein sequences or textual description/captions in scientific publications on the respective biological molecule (e.g. nucleotide, protein). For example, the generated token embeddings may be derived during training the model. The final result (e.g. prediction of next element in sequence) of this first training stage itself may not be of interest. However, the definition of a prediction target may improve the accuracy and/or speed of the training.
- Mapping of images (e.g. images of the respective biological molecule) to the respective token embeddings. In other word, images may be selected of biological structures representing the textual biological input of the training of the language/linguistic model. These images may be used for the second stage training. This mapping of the images might not be necessary, if a database of images with corresponding textual biological description is used.
- Second stage training of an image recognition model (e.g. CNN, Capsule Network) to predict the respective token embeddings found by the first model. Inputs are images of the respective biological molecule. The images may be mapped to the semantics contained in the token embeddings generated by the first model.

For example, token embeddings may be found by building a textual model as shown in FIG. 2. From a repository 200 biological sequences 210 may be passed to a textual model 220 as the independent variable. The textual model may be charged with a task in language processing, such as predicting the next character (e.g. amino acid in protein sequences or base in nucleotide sequences) from a short stretch of the sequence. Other language processing tasks may be possible to find suitable, but different kinds of embeddings. Such tasks can involve homology prediction, predicting the next word in a sentence and others. The data may be passed down an encoder path 230 to learn a hidden representation and through a decoder path to make a useful prediction 250 from it. The hidden representation can be viewed as an embedding (e.g. high dimensional vector) in a latent space. In a trained model this token embedding may represents a mapping of each token to its respective latent vector 260. In a textual model charged with a natural language processing task a token might be the equivalent of a word and a token embedding may be a word embedding.

For example, the visual model is trained to predict token vectors as shown in FIG. 3. From a data repository 300 or a microscope during a running experiment images 310 may be passed as the independent variable to the input of a visual model 320. As the dependent variable the token embeddings 330, which have been mapped to the desired image classes, may be shown to the model at the output. The visual model may learn to predict token embeddings for each input.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm, e.g. a classification algorithm, a regression algorithm or a similarity learning algorithm. Classification algorithms may be used when the outputs are restricted to a limited set of values, i.e. the input is classified to one of the limited set of values. Regression algorithms may be used when the outputs may have any numerical value (within a range). Similarity learning algorithms may be similar to both classification and regression algorithms, but are based on learning from examples using a similarity function that measures how similar or related two objects are. Apart from supervised or semi-supervised learning, unsupervised learning may be used to train the machine-learning model. In unsupervised learning, (only) input data might be supplied, and an unsupervised learning algorithm may be used to find structure in the input data, e.g. by grouping or clustering the input data, finding commonalities in the data. Clustering is the assignment of input data comprising a plurality of input values into subsets (clusters) so that input values within the same cluster are similar according to one or more (predefined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input, but also transform it in a way that makes it useful, often as a pre-processing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge, e.g. based on the training performed by the machine-learning algorithm. In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of the sum of its inputs. The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data, e.g. in classification or regression analysis. Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier. For example, the computer program may be stored on a non-transitory storage medium. Some embodiments relate to a non-transitory storage medium including machine readable instructions, when executed, to implement a method according to the proposed concept or one or more examples described above.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor.

The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100 system for training machine-learning algorithms for processing biology-related data
102 biology-related language-based input training data
104 biology-related image-based input training data
110 one or more processors
120 one or more storage devices
200 database; repository
210 biology-related language-based input training data; biological sequence
220 language recognition machine-learning algorithm; textual model
230 encoder path of language recognition machine-learning algorithm
240 decoder path of language recognition machine-learning algorithm
250 biology-related language-based output training data; prediction
260 first high-dimensional representation; hidden representation; latent vector; token embedding
300 repository
310 biology-related image-based input training data; image
320 visual recognition machine-learning algorithm; visual model
330 second high-dimensional representation; hidden representation; latent vector; token embedding
400 part of a visual recognition neural network; ResNet block
410 batch normalization operation
420 ReLu operation
430 convolution operation
440 adding operation
500 part of a visual recognition neural network; ResNet-CBAM block
510 GlobalAveragePooling operation
520 Global-MaxPooling operation
530 concatenation operation
540 sigmoid operation
550 multiplication operation
560 Mean operation
570 Max operation
600 part of a visual recognition neural network; dense layer with bottleneck configuration
700 part of a visual recognition neural network; dense layer with attention mechanism
800 system for training machine-learning algorithms
810 microscope
820 computer device
900 method for training machine-learning algorithms for processing biology-related data
910 receiving biology-related language-based input training data
920 generating a first high-dimensional representation
930 generating biology-related language-based output training data
940 adjusting the language recognition machine-learning algorithm
950 receiving biology-related image-based input training data
960 generating a second high-dimensional representation

970 adjusting the visual recognition machine-learning algorithm

The invention claimed is:

1. A microscope comprising a system, the system comprising one or more processors and one or more storage devices, wherein the system is configured to:

receive biology-related language-based input training data, wherein the biology-related language-based input training data is a biological sequence;

generate a first high-dimensional representation of the biology-related language-based input training data by a language recognition machine-learning algorithm executed by the one or more processors, wherein the first high-dimensional representation comprises at least three entries each having a different value;

generate biology-related language-based output training data based on the first high-dimensional representation by the language recognition machine-learning algorithm executed by the one or more processors, wherein the biology-related language-based output training data comprises a prediction on a next element in the biological sequence;

adjust the language recognition machine-learning algorithm based on a comparison of the biology-related language-based input training data and the biology-related language-based output training data;

receive biology-related image-based input training data associated with the biology-related language-based input training data from the microscope and generate a second high-dimensional representation of the biology-related image-based input training data by a visual recognition machine-learning algorithm executed by the one or more processors, wherein the second high-dimensional representation comprises at least three entries each having a different value; and adjust the visual recognition machine-learning algorithm based on a comparison of the first high-dimensional representation and the second high-dimensional representation.

2. The system of claim 1, wherein the biology-related image-based input training data is image training data of an image of at least one of a biological structure comprising a nucleotide or a nucleotide sequence, a biological structure comprising a protein or a protein sequence, a biological molecule, a biological tissue, a biological structure with a specific behavior, or a biological structure with a specific biological function or a specific biological activity.

3. The system of claim 1, wherein values of one or more entries of the first high-dimensional representation are proportional to a likelihood of a presence of a specific biological function or a specific biological activity.

4. The system of claim 1, wherein values of one or more entries of the second high-dimensional representation are proportional to a likelihood of a presence of a specific biological function or a specific biological activity.

5. The system of claim 1, wherein the first high-dimensional representation and the second high-dimensional representation are numerical representations.

6. The system of claim 1, wherein the first high-dimensional representation and the second high-dimensional representation each comprise more than 100 dimensions.

7. The system of claim 1, wherein the first high-dimensional representation is a first vector and the second high-dimensional representation is a second vector.

8. The system of claim 1, wherein more than 50% of values of the entries of the first high-dimensional representation and more than 50% of values of the entries of the second high-dimensional representation are non-zero.

9. The system of claim 1, wherein the values of more than 5 entries of the first high-dimensional representation are larger than 10% of a largest absolute value of the entries of the first high-dimensional representation and the values of more than 5 entries of the second high-dimensional representation are larger than 10% of a largest absolute value of the entries of the second high-dimensional representation.

10. The system of claim 1, wherein the comparison of the biology-related language-based input training data and the biology-related language-based output training data for the adjustment of the language recognition machine-learning algorithm is based on a cross entropy loss function.

11. The system of claim 1, wherein the comparison of the first high-dimensional representation and the second high-dimensional representation for the adjustment of the visual recognition machine-learning algorithm is based on a cosine similarity loss function.

12. The system of claim 1, wherein the biology-related language-based input training data comprises a length of more than 20 characters.

13. The system of claim 1, wherein the adjustment of the language recognition machine-learning algorithm comprises an adjustment of a plurality of language recognition neural network weights, wherein a final set of language recognition neural network weights is stored by the one or more storage devices.

14. The system of claim 1, wherein the adjustment of the visual recognition machine-learning algorithm comprises an adjustment of a plurality of visual recognition neural network weights, wherein a final set of visual neural network weights is stored by the one or more storage devices.

15. The system of claim 1, wherein the language recognition machine-learning algorithm comprises a language recognition neural network.

16. The system of claim 15, wherein the language recognition neural network comprises more than 30 layers.

17. The system of claim 15, wherein the language recognition neural network is a recurrent neural network.

18. The system of claim 15, wherein the language recognition neural network is a long short-term memory network.

19. The system of claim 1, wherein the visual recognition machine-learning algorithm comprises a visual recognition neural network.

20. The system of claim 19, wherein the visual recognition neural network comprises more than 30 layers.

21. The system of claim 19, wherein the visual recognition neural network is a convolutional neural network or a capsule network.

22. The system of claim 19, wherein the visual recognition neural network comprises a plurality of convolution layers and a plurality of pooling layers.

23. The system of claim 19, wherein the visual recognition neural network uses a rectified linear unit activation function.

24. The system of claim 1, wherein the system is configured to repeat, for each biology-related language-based input training data of a training group of biology-related language-based input training data sets, the steps of:

generating the first high-dimensional representation, generating the biology-related language-based output training data, and adjusting the language recognition machine-learning algorithm.

25. The system of claim 24, wherein a length of the first biology-related language-based input training data of the training group of biology-related language-based input training data sets differs from a length of second biology-related language-based input training data of the training group of biology-related language-based input training data sets.

26. The system of claim 1, wherein the system is configured to repeat, for each biology-related image-based input training data of a training group of biology-related image-based input training data sets, the steps of:

generating a second high-dimensional representation, and adjusting the visual recognition machine-learning algorithm.

27. The system of claim 26, wherein the training group of biology-related language-based input training data sets comprises more entries than the training group of biology-related image-based input training data sets.

28. A method for training machine-learning algorithms for processing biology-related data using a microscope, the method comprising:

receiving biology-related language-based input training data, wherein the biology-related language-based input training data is a biological sequence;

generating a first high-dimensional representation of the biology-related language-based input training data by a language recognition machine-learning algorithm, wherein the first high-dimensional representation comprises at least three entries each having a different value;

generating biology-related language-based output training data based on the first high-dimensional representation by the language recognition machine-learning algorithm, wherein the biology-related language-based output training data comprises a prediction on a next element in the biological sequence;

adjusting the language recognition machine-learning algorithm based on a comparison of the biology-related language-based input training data and the biology-related language-based output training data;

receiving biology-related image-based input training data associated with the biology-related language-based input training data from the microscope;

generating a second high-dimensional representation of the biology-related image-based input training data by a visual recognition machine-learning algorithm, wherein the second high-dimensional representation comprises at least three entries each having a different value; and adjusting the visual recognition machine-learning algorithm based on a comparison of the first high-dimensional representation and the second high-dimensional representation.

29. A non-transitory, computer-readable medium storing a trained machine learning algorithm, the trained machine learning algorithm trained by:

receiving biology-related language-based input training data, wherein the biology-related language-based input training data is a biological sequence;

generating a first high-dimensional representation of the biology-related language-based input training data by a language recognition machine-learning algorithm, wherein the first high-dimensional representation comprises at least three entries each having a different value;

generating biology-related language-based output training data based on the first high-dimensional representation by the language recognition machine-learning algorithm, wherein the biology-related language-based output training data comprises a prediction on a next element in the biological sequence;

adjusting the language recognition machine-learning algorithm based on a comparison of the biology-related language-based input training data and the biology-related language-based output training data;

receiving biology-related image-based input training data associated with the biology-related language-based input training data from a microscope;

generating a second high-dimensional representation of the biology-related image-based input training data by a visual recognition machine-learning algorithm, wherein the second high-dimensional representation comprises at least three entries each having a different value; and adjusting the visual recognition machine-learning algorithm based on a comparison of the first high-dimensional representation and the second high-dimensional representation.

* * * * *